United States Patent [19]

Kinoshita et al.

[11] Patent Number: 5,374,429
[45] Date of Patent: Dec. 20, 1994

[54] MEDICAL ADHESIVE SHEET AND MEDICAL PREPARATION

[75] Inventors: Takashi Kinoshita; Saburo Otsuka; Hitoshi Akemi; Kazuhiro Higashio, all of Osaka, Japan

[73] Assignee: Nitto Denko Corporation, Osaka, Japan

[21] Appl. No.: 46,962

[22] Filed: Apr. 16, 1993

[30] Foreign Application Priority Data

May 12, 1992 [JP] Japan .................................. 4-146328

[51] Int. Cl.$^5$ ............................................. A61F 13/02
[52] U.S. Cl. .................................. 424/448; 424/443; 424/449
[58] Field of Search ..................... 424/448, 449, 443

[56] References Cited

U.S. PATENT DOCUMENTS 4,915,950 4/1990 Miranda et al. .................. 424/448
5,225,199 7/1993 Hidaka et al. .................... 424/448

Primary Examiner—G. S. Kishore
Assistant Examiner—Amy L. Hulina
Attorney, Agent, or Firm—Sughrue, Mion, Zinn, Macpeak & Seas

[57] ABSTRACT

A medical adhesive sheet comprising a support comprising a laminate of a polyester film having a thickness of from 0.5 to 6 μm and a polyester nonwoven fabric having a basis weight of from 5 to 20 g/m², and a pressure-sensitive adhesive layer laminated on the surface of the nonwoven fabric.

14 Claims, No Drawings

MEDICAL ADHESIVE SHEET AND MEDICAL PREPARATION

FIELD OF THE INVENTION

The present invention relates to a medical adhesive sheet used by adhering to a skin surface and also to a medical preparation containing a drug. More particularly, the present invention relates to a medical adhesive sheet and a medical preparation each having a good anchoring property between a pressure-sensitive adhesive layer and a support and a good handling property at adhering operation, and also having an excellent feeling of use at adhering in spite of a thin support.

BACKGROUND OF THE INVENTION

A medical adhesive sheet used by adhering to a skin surface is used for various uses as a medical adhesive sheet for covering to protect skin surfaces, a medical preparation for percutaneously admistrating a drug into a body. However, since the surface to be adhered is a skin surface, at the development thereof, the handling property at adhering, the follow-up property (flexibility) to the movement of the skin surface, non-irritative property to the skin, etc., are important required characteristics. Also, in a medical preparation, the characteristics such as the impermeability of a drug from the back surface of the support, a drug releasing property, etc., are required. In particular, such a medical adhesive sheet is sometimes in an adhered state for a relatively long period of time and in such a case, the medical adhesive sheet showing no feeling of discomfort after adhering to the skin surface and giving no irritativeness to the skin is considered to have important required characteristics.

For meeting such requirements, a medical adhesive sheet wherein the thickness of the support is reduced as thin as possible, whereby the irritativeness by the edge portions of the support is reduced and further the skin follow-up property is imparted has been proposed. However, when the thickness of the support is thinned, although the above required characteristics can be satisfied, the medical adhesive sheet itself loses the self-supporting property, causing the problems that the handling property at adhering is reduced, after adhering, the medical adhesive sheet creases and also the adhering surfaces adhere to each other at adhering, whereby the medical adhesive sheet cannot be finely adhered.

Thus, to overcome the above problems, a medical adhesive sheet wherein a pasteboard having a self-supporting property is temporarily bonded to the back surface of a support film having a thin thickness and a medical adhesive sheet wherein a material having a flexibility, such as a polyurethane film, etc., is used as the material for the support itself and the thickness of the support is increased to some extent to improve the handling property have been proposed.

The former medical adhesive sheet is described in JP-A-55-32553, JP-A-64-16719 (the term "JP-A" as used herein means an "unexamined published Japanese patent application"), JP-A-U-56-57235, JP-A-U-56-158215 (the term "JP-A-U" as used herein means an "unexamined published Japanese utility model application"), etc., and is excellent in operability at adhering. However, in the medical adhesive sheet, if the control of the adhesive force at temporarily bonding the self-supporting pasteboard is insufficient, it sometimes happens that the pasteboard is released before adhering the medical adhesive sheet and also in separating the pasteboard after adhering, the medical adhesive sheet itself is also separated. Thus, it is necessary that the adhesive force for temporary adhering is controlled with a sufficient care. Also, in this case, since the surface of the support film is relatively smooth, the adhesive force (anchoring force) to a pressure-sensitive adhesive layer becomes sometimes weak, and as a result, when the medical adhesive sheet is separated from the skin surface, there is a possibility of causing a so-called adhesive remaining phenomenon that the pressure-sensitive adhesive remains on the skin surface.

On the other hand, in the latter medical adhesive sheet, although the material for the support is a soft material, since the thickness of the support is increased, it sometimes happens that in the case of adhering the medical adhesive sheet for a long period of time, the irritativeness by the edge portions of the support cannot be sufficiently reduced.

In particular, in a medical preparation containing a drug which is percutaneously absorbed into the body by strictly controlling the doses of the drug, the improvement of the handling property and the reduction of the skin irritativeness described above are important problems to be overcome and the development of the technique which can overcome these problems has been actually desired.

SUMMARY OF THE INVENTION

As a result of various investigations to overcome the above-described problems, the inventors have discovered that by using a support formed by laminating a plastic nonwoven fabric having a relatively small basis weight onto a thin plastic film having no self-supporting property, the skin irritative property can be reduced. It has also been discovered that by using polyester as the material for the plastic film and plastic nonwoven fabric and forming a pressure-sensitive adhesive layer at the nonwoven fabric side, the anchoring force between the support and the adhesive layer increases and when a drug is incorporated in the adhesive layer to provide a medical preparation, a strike-through phenomenon that the drug permeates through the back surface of the support can be completely prevented. The present invention has been accomplished based on those findings.

Accordingly, one object of the present invention is to provide a medical adhesive sheet.

Another object of the present invention is to provide a medical preparation containing a drug.

According to one embodiment of the present invention, there is provided a medical adhesive sheet comprising a support comprising a laminate of a polyester film having a thickness of 0.5 $\mu$m to 6 $\mu$m and a polyester nonwoven fabric having a basis weight of from 5 to 20 $g/m^2$, and a pressure-sensitive adhesive layer laminated on the surface of the nonwoven fabric of the support.

According to another embodiment of the present invention, there is provided a medical preparation formed by incorporating a drug in the adhesive layer of the above-described medical adhesive sheet.

DETAILED DESCRIPTION OF THE INVENTION

The present invention is described in detail below.

The medical adhesive sheet of the present invention has the feature in the constitution of the support which comprises a laminate of a polyester film having a thickness of 0.5 to 6 μm and a polyester nonwoven fabric having a basis weight of from 5 to 20 g/m². The polyester film is preferably as thin as possible for reducing the irritation by the edges of the support and from the point of practical use, it is preferred to use a very thin polyester film having a thickness of from 1 to 4 μm, and more preferably from 2 to 3 μm. If the thickness of the film is thinner than 0.5 μm, it becomes difficult to obtain the support of the present invention by laminating with the nonwoven fabric described below. Hence such a too thin film is unsuitable for practical use and also if the thickness of the polyester film is over 6 μm, the rigidity of the polyester itself is revealed and when the medical adhesive sheet is adhered to the skin surface, it gives a stiff feeling (a feeling of discomfort).

Also, in the present invention, to prevent the occurrence of the stiff feeling after adhering to the skin surface and to improve the anchoring property to the adhesive layer laminated, it is necessary that the basis weight of the polyester nonwoven fabric laminated with the above-described polyester film is less than that of conventional nonwoven fabrics. The basis weight of the polyester nonwoven fabric used in the present invention is preferably from 8 to 15 g/m², and more preferably from 10 to 12 g/m². If the basis weight thereof is less than 5 g/m², when the polyester nonwoven fabric is laminated with the polyester film, the function and the effect as the nonwoven fabric and the improvement of the anchoring property to the adhesive layer are not sufficiently obtained, and if the basis weight is over 20 g/m², the nonwoven fabric gives a stiff feeling.

The polyester nonwoven fabric used in the present invention is neither a woven fabric nor knitted fabric having gaps by a weaving machine or a knitting machine but is prepared by mechanically uniformly uniting polyester fibers by twisting, etc. Hence the anchoring property in the case of forming the adhesive layer is good, which is preferable.

As the polyester which is used for the polyester film and the polyester nonwoven fabric described above, a material comprising polyethylene terephthalate is preferred from the points of safety (non-toxicity) to a living body, practical uses, wide uses, etc. Practically, an ethylene terephthlate homopolymer, a copolymer containing an ethylene terephthalate unit as the main unit and other ester unit(s), and a mixture of an ethylene terephthalate homopolymer and a polymer or polymers comprising other ester unit(s) can be used.

As the other ester unit which is used to form the above-described ethylene terephthalate copolymer or the mixture with the ethylene terephthalate homopolymer, an aromatic dicarboxylic acid such as isophthalic acid, diphenyldicarboxylic acid, diphenyl ether dicarboxylic acid, diphenylsulfonedicarboxylic acid, naphthalenedicarboxylic acid, etc.; or an aliphatic dicarboxylic acid such as adipic acid, sebacic acid, etc.; can be used as a dicarboxylic acid unit and also an alkylene glycol such as trimethylene glycol, tetramethylene glycol, hexamethylene glycol, etc.; an aromatic diol such as hydroquinone, resorcinol, bisphenol A, etc.; an aliphatic diol such as bis(hydroxyethoxyphenyl)sulfone, bis(hydroxyethoxyphenyl)propane, etc.; diethylene glycol, etc., can be used as a diol component.

The support for the medical adhesive sheet and the medical preparation of the present invention comprises a laminate of the specific polyester film and polyester nonwoven fabric as described above and they can be laminated by, for example, coating an optional adhesive on the film side by a gravure coater, etc., at a dry coated amount of from about 1 to 3 g/m² and press-bonding the nonwoven fabric to the film, if necessary, by heating. As the adhesive used, there are conventional adhesives such as a polyester series adhesive, an acrylic adhesive, a vinyl chloride series adhesive, vinyl acetate series adhesive, a rubber series adhesive, a urethane series adhesive, etc., can be used, but from the points of the anchoring property with the adhesive layer and the impermeability of a drug in the case of using the adhesive layer containing the drug, it is preferred that a polyester is used for all the materials of the support and the polyester series adhesive is used as the adhesive for forming the support.

In addition, the laminate structure of the support in the present invention is not always a double layer structure but may be a multilayer structure having the polyester nonwoven fabric layer on at least one surface and may be a three-layer structure of, for example, nonwoven fabric (or foamed product)/film/nonwoven fabric. It is preferable to laminate the nonwoven fabric layer or the foamed product to the back surface of the support as described above since at adhering the medical adhesive sheet to the skin surface, the sheet gives an appropriate feeling and a deluxe feeling to a person who is adhered with the medical adhesive sheet.

The medical adhesive sheet of the present invention has a pressure-sensitive adhesive layer formed at the nonwoven fabric surface side of the support. As the pressure-sensitive adhesive for the pressure-sensitive adhesive layer formed, any pressure-sensitive adhesives such as acrylic adhesives, natural rubber adhesives, synthetic rubber adhesives, vinyl ether series adhesives, silicone series adhesives, etc., can be used if they are adhesives for medical use and do not have a skin irritative property since the adhesive itself is contacted with the skin surface. In these adhesives, from the points of the stability of the quality the easiness of controlling the adhesive force, the releasing property of a drug, etc., an acrylic adhesive obtained by polymerizing 50% by weight or more of (meth)acrylic acid alkyl ester can be preferably used. Also, for giving a soft feeling to reduce the irritative property at adhering the medical adhesive sheet to the skin surface, the adhesive layer may further contain from about 0.1 to 60% by weight, and preferably from about 30 to 50% by weight, based on the weight of the adhesive layer of an organic liquid component compatible with the adhesive component and, if necessary, may be subjected to a crosslinking treatment.

In the medical adhesive sheet and the medical preparation of the present invention, it is preferred to use a viscoelastic pressure-sensitive adhesive layer showing an elongation per unit area of from 300 to 2,000%/mm², and preferably from 500 to 1,500%/mm², at the breakage at a tensile speed of 50 mm/min. Since the adhesive layer having the above-described properties has a viscoelasticity and a weaker adhesive force than a pressure-sensitive adhesive layer used for a conventional medical adhesive sheet, the problems of reducing the anchoring property with the support, causing an adhesive remaining phenomenon, and oozing the adhesive from the side of the support to stain the skin surface, tend to occur. Accordingly, the present invention can exhibit, by laminating such an adhesive layer to the nonwoven fabric surface of the support described above, the effect of greatly improving the anchoring property by the adhesive layer which bites into the nonwoven fabric.

Also, by incorporating a drug in the pressure-sensitive adhesive layer in the present invention, a medical preparation for the percutaneous absorption for the prophylaxis and the treatment of various diseases can be prepared. Any local drugs and systemic drugs can be used as such a drug if these drugs show a medical effect by being percutaneously absorbed. Examples of the drugs which can be practically used are corticostroids, an analgestic anti-inflammatory agent, a hypnitic sedative, a tranquilizer, an antihypertensive agent, a hypotensive diuretic, antibiotics, an anesthetic, an antibacterial agent, an antifungal agent, vitamins, a coronary dilator agent, an antihistamine, an antitussive agent, a sex hormone, an antidepression agent, a cerebral circulation improving agent, an antiemetic agent, an antitumor agent, vital medicaments, etc. If necessary, two or more kinds of these drugs can be incorporated together in the adhesive layer.

The content of the drug can be properly selected according to the kind of the drug and the purpose of the administration thereof but the drug is incorporated in the adhesive layer in an amount of usually from about 1 to 40% by weight, and preferably from about 2 to 30% by weight, based on the weight of the adhesive layer. If the content thereof is less than 1% by weight, the release of the effective amount of the drug for the therapy of a disease cannot be expected. If the content is over 40% by weight, the therapeutical effect is not further increased and the use of such a large amount of drug is economically disadvantageous.

Since as described above, the medical adhesive sheet of the present invention uses the support having the structure that a polyester nonwoven fabric of a specific basis weight is laminated to a very thin polyester film, the medical adhesive sheet has a proper self-supporting property at adhering operation and is excellent in handling property. The sheet also shows the effect capable of remarkably reducing the skin irritative property after adhering.

Also, in the medical preparation obtained by incorporating a drug in the adhesive layer of the medical adhesive sheet, the drug does not permeate to the back surface of the support, whereby the content of the drug does not reduce during the storage of the medical preparation and thus the medical preparation can give the expected medical effect.

The invention is described more practically by the following examples, wherein all parts and %, unless otherwise indicated, are by weight.

EXAMPLE 1

After mixing 40 parts of isopropyl myristate and 60 parts (as solid components) of an aqueous solution of an acrylic adhesive obtained by copolymerizing 97 parts of acrylic acid nonyl ester and 3 parts of acrylic acid in an organic solvent, 0.2 part of a trifunctional isocyanate was added to 99.8 parts of the solid components of the adhesive to carry out the crosslinking treatment.

The adhesive solution thus obtained was coated on a separator at a dry thickness of 60 $\mu$m followed by drying to form an adhesive layer. The elongation of the adhesive layer per unit area at breaking at a tensile speed of 50 mm/min was 1,100%/mm$^2$.

The adhesive layer prepared as described above was transferred onto a polyethylene terephthalate nonwoven fabric of a laminate of polyethylene terephthlate (thickness 2 $\mu$m) and the polyethylene terephthalate nonwoven fabric (basis weight 8 g/m$^2$) as a support followed by press-bonding to provide a medical adhesive sheet of the present invention.

EXAMPLE 2

To 40 parts of the solid components of the aqueous solution of the acrylic adhesive obtained in Example 1 were added 40 parts of isopropyl myristate and 20 parts of isosorbide dinitrate followed by mixing and the crosslinking treatment was carried out in the same manner as in Example 1 to provide a medical preparation.

The elongation of the adhesive layer of the medical preparation per unit area at breaking at a tensile speed of 50 mm/min. was 1,200%/mm$^2$.

Comparative Example 1

By following the same procedure as in Example 1 except that a polyethylene terephthalate film with a thickness of 6 $\mu$m was used as the support, a medical adhesive sheet without having the nonwoven fabric layer was prepared.

Comparative Example 2

By following the same procedure as in Example 1 except that a polyethylene terephthalate film having a thickness of 25 $\mu$m was used as the support, a medical adhesive sheet without having the nonwoven fabric layer was prepared.

Comparative Example 3

By following the same procedure as in Example 2 except that a laminate of a polyethylene terephthalate film having a thickness of 3 $\mu$m and an ethylene-vinyl acetate copolymer film having a thickness of 20 $\mu$m was used as the support and the adhesive layer was then laminated on the side of the ethylene-vinyl acetate copolymer film, a medical preparation was prepared.

Comparative Example 4

By following the same procedure as in Example 1 except that a laminate of a polyethylene terephthalate film having a thickness of 8 $\mu$m and a polyethylene terephthalate nonwoven fabric having a basis weight of 8 g/m$^2$ was used as the support, a medical adhesive sheet was prepared.

Comparative Example 5

By following the same procedure as in Example 1 except that a polyethylene film having a thickness of 50 $\mu$m was used as the support, a medical adhesive sheet without having the nonwoven fabric layer was prepared.

Comparative Example 6

By following the same procedure as in Example 2 except that a polyethylene terephthalate nonwoven fabric having a basis weight of 30 g/m$^2$ was used as the support, a medical preparation was prepared.

Comparative Example 7

By following the same procedure as in Example 1 except that the adhesive layer transferred onto not the nonwoven fabric surface but the polyethylene terephthalate film surface, a medical adhesive sheet was prepared.

EXAMPLE 3

After mixing 35 parts of octyl palmitate with 65 parts of the solid components of an aqueous solution of an acrylic adhesive obtained by copolymerizing 80 parts of acrylic acid butyl ester, 17 parts of methacrylic acid methyl ester, and 3 parts of acrylic acid, 0.4 part of ethyl acetoacetate aluminum diisopropylate was added to 99.5 parts of the solid components of the adhesive to carry out the crosslinking treatment.

The adhesive solution thus obtained was coated on a separator at a dry thickness of 60 μm followed by drying to form an adhesive layer. The elongation of the adhesive layer per unit area at breaking at a tensile speed of 50 mm/min. was 500%/mm$^2$.

The adhesive layer prepared as described above was transferred onto the surface of a polyethylene terephthalate nonwoven fabric of a laminate of a polyethylene terephthalate film (thickness 2 μm) and the polyethylene terephthalate nonwoven fabric (basis weight 12 g/m$^2$) as a support followed by press-bonding to provide a medical adhesive sheet of the present invention.

EXAMPLE 4

To 60 parts of the solution of the acrylic adhesive obtained in Example 3 were added 20 parts of octyl palmitate and 20 parts of metoprolol followed by mixing and the crosslinking treatment was carried out in the same manner as in Example 3. Thereafter, by following the same procedure as in Example 3 using the adhesive layer thus formed, a medical preparation of the present invention was obtained.

The elongation of the adhesive layer per unit area at breaking at a tensile speed of 50 mm/min. was 400%/mm$^2$.

Comparative Example 8

By following the same procedure as in Example 3 except that an ethylene-vinyl acetate copolymer film having a thickness of 50 μm was used as the support, a medical adhesive sheet was prepared.

Comparative Example 9

By following the same procedure as in Example 4 except that a laminate of a polyethylene terephthalate film (thickness 6 μm) and an ethylene-vinyl acetate copolymer film (thickness 20 μm) was used as the support and the adhesive layer was laminated to the side of the ethylene-vinyl acetate copolymer film, a medical preparation was obtained.

EXAMPLE 5

The solution of the acrylic adhesive obtained in Example 1 was coated as it was on a separator at a dry thickness of 60 μm followed by drying to provide an adhesive layer.

When the elongation of the adhesive layer per unit area at breaking at a tensile speed of 50 mm/min. was measured, the adhesive layer was not broken even at above 2,000%.

The adhesive layer was transferred onto the nonwoven fabric surface of the same laminated support as in Example 1 followed by press-bonding to provide a medical adhesive sheet of the present invention.

Each of the medical adhesive sheets and the medical preparations obtained in the examples and the comparative examples described above was subjected to the following tests. The results obtained are shown in Table 1 and Table 2.

[Handling Property]

Each sample cut into a size of 25 cm$^2$ was adhered to the hind arm side of each of 6 persons, the handling property at the side was evaluated by the following standards (ranks), and the average value was determined.

3: At adhering, the sample can be finely adhered without causing adhering of the adhesive layer surfaces to each other.

2: The sample can be finely adhered but there is some difficulty in the handling property.

1: The sample creases at adhering and the adhesive layer surfaces are adhered to each other, thereby the sample is reluctant to handle.

[Adhesion Feeling]

Each sample cut into a size of 10 cm$^2$ was adhered to the breast of each of 6 persons, the adhesion feeling was evaluated by the following standards, and the average value was determined.

3: The adhesion feeling is good and shows no feeling of discomfort.

2: The sample shows a slight feeling of discomfort.

1: The sample shows a considerable feeling of discomfort.

[Anchoring Property]

After carrying out the above adhesion feeling test, each sample was separated from the skin surface, the anchoring property between the support and the adhesive layer was evaluated by the following standards, and the average value was determined.

3: The anchoring property is good and the adhesive does not remain on the skin surface.

2: Some residue of the adhesive is observed at the circumference of the adhered portion of the skin.

1: The anchoring property is poor and the residue of the adhesive is observed at almost the entire adhered portion of the skin.

[Skin Non-irritative Property]

After removing each sample from the skin surface in the above anchoring test, the skin surface was observed after 60 minutes since then. The extent of the skin irritative property was evaluated by the following standards and the average value was determined.

3: Almost same as the state of the skin surface before adhering the sample.

2: A slight erythema occurs.

1: A clear erythema occurs.

[Change of Appearance]

Each sample cut into a size of 25 cm$^2$ was tightly enclosed in a packaging material and after storing it for one month under the conditions of 40° C. and 75% in humidity, the change of the appearance before and after storing was determined by the following standards.

3: Almost no change occurs before and after storing.

2: Changes of causing slight curling, etc., occur after storing.

1: The support is swelled to considerably change the appearance after storing.

[Residual Drug]

Each sample (Three samples were used for the average value.) of the medical preparations cut into a size of 25 cm$^2$ was tightly enclosed in a packaging material and after storing it for 3 months under the conditions of 40° C. and 75% in humidity, the amount of the drug remained in the medical preparation was determined. The content of the drug in the medical preparation before storing was defined as 100% and the amount of residual drug was calculated from the content of the drug after storing.

TABLE 1

| Example | Handling Property | Adhesion Feeling | Anchoring Property | Skin Non-irritative Property | Change of Appearance | Residual Drug (%) |
| --- | --- | --- | --- | --- | --- | --- |
| 1 | 3 | 3 | 3 | 3 | 3 | — |
| 2 | 3 | 3 | 3 | 3 | 3 | 99.6 |
| 3 | 3 | 3 | 3 | 3 | 3 | — |
| 4 | 3 | 2 | 3 | 2 | 3 | 99.8 |
| 5 | 3 | 2 | 3 | 2 | 3 | — |

TABLE 2

| Comparative Example | Handling Property | Adhesion Feeling | Anchoring Property | Skin Non-irritative Property | Change of Appearance | Residual Drug (%) |
| --- | --- | --- | --- | --- | --- | --- |
| 1 | 1 | 3 | 2 | 3 | 3 | — |
| 2 | 3 | 2 | 2 | 2 | 3 | — |
| 3 | 2 | 3 | 3 | 3 | 1 | 97.6 |
| 4 | 3 | 1 | 3 | 2 | 3 | — |
| 5 | 3 | 2 | 2 | 3 | 2 | — |
| 6 | 3 | 1 | 3 | 3 | 3 | 98.2 |
| 7 | 3 | 2 | 2 | 3 | 3 | — |
| 8 | 3 | 3 | 3 | 3 | 1 | 89.1 |
| 9 | 3 | 3 | 3 | 2 | 1 | 89.1 |

While the invention has been described in detail and with reference to specific examples thereof, it will be apparent to one skilled in the art that various changes and modifications can be made therein without departing from the spirit and scope thereof.

What is claimed is:

1. A medical preparation comprising a support comprising a laminate of a polyester film having a thickness of from 0.5 to 6 μm and a polyester nonwoven fabric having a basis weight of from 5 to 20 g/m², and a pressure-sensitive adhesive layer laminated on the surface of the nonwoven fabric, said adhesive layer containing a drug.

2. The medical preparation of claim 1, wherein the amount of the drug is from 1 to 40% by weight based on the weight of the adhesive layer.

3. The medical preparation of claim 1, wherein the amount of the drug is from 2 to 30% by weight based on the weight of the adhesive layer.

4. The medical preparation of claim 1, wherein the polyester film has a thickness of from 1 to 4 μm.

5. The medical preparation of claim 1, wherein the polyester film has a thickness of from 2 to 3 μm.

6. The medical preparation of claim 1, wherein the polyester nonwoven fabric has a basis weight of from 8 to 15 m/g².

7. The medical preparation of claim 1, wherein the polyester nonwoven fabric has a basis weight of from 10 to 12 m/g².

8. The medical preparation of claim 1, wherein the polyester film is laminated to the polyester nonwoven fabric with an adhesive.

9. The medical preparation of claim 8, wherein the adhesive is a polyester series adhesive.

10. The medical preparation of claim 1, wherein the pressure-sensitive adhesive layer is an acrylic pressure-sensitive adhesive obtained by polymerizing 50% by weight or more of (meth)acrylic acid alkyl ester.

11. The medical preparation of claim 1, wherein the pressure-sensitive adhesive contains from 0.1 to 60% by weight of an organic liquid component compatible with the pressure-sensitive adhesive.

12. The medical preparation of claim 1, wherein the pressure-sensitive adhesive is subjected to crosslinking treatment.

13. The medical preparation of claim 1, wherein the pressure-sensitive adhesive layer is a viscoelastic pressure-sensitive adhesive layer showing an elongation per unit area at breakage at a tensile speed of 50 mm/min. of from 300 to 2,000%/mm².

14. The medical preparation of claim 13, wherein the elongation is from 500 to 1,500%/mm².

* * * * *